(12) United States Patent
Adamczyk et al.

(10) Patent No.: US 9,757,511 B2
(45) Date of Patent: Sep. 12, 2017

(54) PERSONAL MEDICAL DEVICE AND METHOD OF USE WITH RESTRICTED MODE CHALLENGE

(71) Applicant: MEDTRONIC MINIMED, INC., Northridge, CA (US)

(72) Inventors: Robert G. Adamczyk, Tarzana, CA (US); Mark Freger, Los Angeles, CA (US); David P. Lewinski, Chagrin Falls, OH (US); Ulrich H. Rankers, Porter Ranch, CA (US); Lisa M. Val Verde, Los Angeles, CA (US); Steven J. Vargas, San Fernando, CA (US); Yongbo Wang, Arcadia, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 14/886,451

(22) Filed: Oct. 19, 2015

(65) Prior Publication Data

US 2017/0106139 A1   Apr. 20, 2017

(51) Int. Cl.
*G08B 21/00* (2006.01)
*A61M 5/142* (2006.01)
*G06F 3/0489* (2013.01)
*A61M 5/172* (2006.01)

(52) U.S. Cl.
CPC ...... *A61M 5/14244* (2013.01); *A61M 5/1723* (2013.01); *G06F 3/04895* (2013.01); *A61M 2205/505* (2013.01); *A61M 2205/52* (2013.01); *A61M 2205/583* (2013.01); *A61M 2205/6009* (2013.01); *A61M 2230/201* (2013.01)

(58) Field of Classification Search
CPC ................ A61M 5/142; A61M 5/1723; A61M 5/14244; G06F 19/3468; G06F 3/0488; G09B 21/00
USPC ......................................................... 340/5.32
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |

(Continued)

*Primary Examiner* — Mark Rushing
(74) *Attorney, Agent, or Firm* — Medtronic Minimed, Inc.

(57) ABSTRACT

A personal medical device and method of use with restricted mode challenge having a personal medical device including: a memory operable to store programming code; a processor operably connected to the memory; a user input having input buttons to receive input from the user; and a user display to display output to the user. The processor is operable to: detect a user request for entry to the restricted mode; display a user input image on the user display, the user input image including display buttons corresponding to the input buttons; highlight one of the display buttons; detect actuation of one of the input buttons on the user input; and deny entry to the restricted mode when the one of the input buttons does not correspond to the highlighted display button.

17 Claims, 12 Drawing Sheets

(56) References Cited

U.S. PATENT DOCUMENTS

| | | | |
|---|---|---|---|
| 6,049,328 A * | 4/2000 | Vanderheiden | G09B 21/00 341/21 |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 7,990,251 B1 * | 8/2011 | Ford, Jr. | G06F 3/04847 340/286.01 |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2007/0123819 A1 | 5/2007 | Mernoe et al. | |
| 2010/0160861 A1 | 6/2010 | Causey, III et al. | |
| 2010/0198142 A1 * | 8/2010 | Sloan | A61B 5/14532 604/66 |
| 2014/0325065 A1 * | 10/2014 | Birtwhistle | H04L 47/70 709/225 |
| 2015/0025498 A1 * | 1/2015 | Estes | A61M 5/14244 604/506 |

\* cited by examiner

PERSONAL MEDICAL DEVICE AND METHOD OF USE WITH RESTRICTED MODE CHALLENGE

TECHNICAL FIELD

The technical field of this disclosure is personal medical systems, particularly, personal medical devices and methods of use with restricted mode challenge.

BACKGROUND OF THE INVENTION

Advances in electronics have resulted in the miniaturization of medical devices such that medical devices which previously required large stationary equipment can now be worn about the person, who can be monitored or receive treatment while pursuing normal daily tasks.

One area of such advances has been in the treatment of diabetes. An estimated twenty-six million people in the United States, or about 8% of the population, have diabetes. This percentage is expected to increase in the near-term as the population ages. Wearable glucose monitors and insulin pumps have been developed which allow persons under treatment for diabetes to be monitored and receive insulin while carrying on their day-to-day tasks.

Unfortunately, advances in insulin delivery to improve treatment can also create new problems when the user enters a restricted mode to program the insulin delivery, such as basal or bolus infusions. One problem arises when a user becomes overly familiar with the programming procedure and resorts to a series of memorized keystrokes: the user presses keys without monitoring the visual display of the insulin pump to confirm that they are programming the insulin pump as they desire. Such behavior can arise when the user is shy about displaying the insulin pump in public where it can draw attention. Another problem arises when inadvertent contact with the insulin pump controls results in unintended delivery, suspension, or resumption of insulin administration. Yet another problem arises when a user attempts to program the insulin pump from memory, even though the visual display is inoperable and no longer displays user input parameters.

It would be desirable to have a personal medical device and method of use with restricted mode challenge that would overcome the above disadvantages.

SUMMARY OF THE INVENTION

One aspect of the invention provides a personal medical device for employment by a user and having a restricted mode, the medical device including: a memory operable to store programming code; a processor operably connected to the memory; a user input operably connected to the processor and having input buttons to receive input from the user; and a user display operably connected to the processor to display output to the user. The processor is responsive to the programming code to: detect a user request for entry to the restricted mode; display a user input image on the user display in response to the detected user request, the user input image including display buttons corresponding to the input buttons; highlight one of the display buttons; detect actuation of one of the input buttons on the user input; and deny entry to the restricted mode when the one of the input buttons does not correspond to the highlighted one of the display buttons.

Another aspect of the invention provides a personal medical system for providing a therapeutic fluid to a user, the personal medical system including: a reservoir containing the therapeutic fluid; a personal medical device having a restricted mode, the personal medical device being operably connected to the reservoir to receive the therapeutic fluid; and an infusion set operably connected to the personal medical device to receive the therapeutic fluid. The personal medical device further includes a memory operable to store programming code; a processor operably connected to the memory; a user input operably connected to the processor and having input buttons to receive input from the user; a user display operably connected to the processor to display output to the user; and a fluid driver in fluid communication between the reservoir and the infusion set, the fluid driver being responsive to a flow control signal from the processor to drive the therapeutic fluid from the reservoir to the user through the infusion set. The processor is responsive to the programming code to: detect a user request for entry to the restricted mode; display a user input image on the user display in response to the detected user request, the user input image including display buttons corresponding to the input buttons; highlight one of the display buttons; detect actuation of one of the input buttons on the user input; and deny entry to the restricted mode when the one of the input buttons does not correspond to the highlighted one of the display buttons.

Yet another aspect of the invention provides a method of use for a personal medical device having a user display and a user input, the user input having a plurality of input buttons, the method including detecting a user request for entry to a restricted mode of the personal medical device; displaying a user input image on the user display in response to the detected user request, the user input image including display buttons corresponding to the input buttons; highlighting one of the display buttons; detecting actuation of one of the input buttons on the user input; and denying entry to the restricted mode when the one of the input buttons does not correspond to the highlighted one of the display buttons.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION

Figure 1:
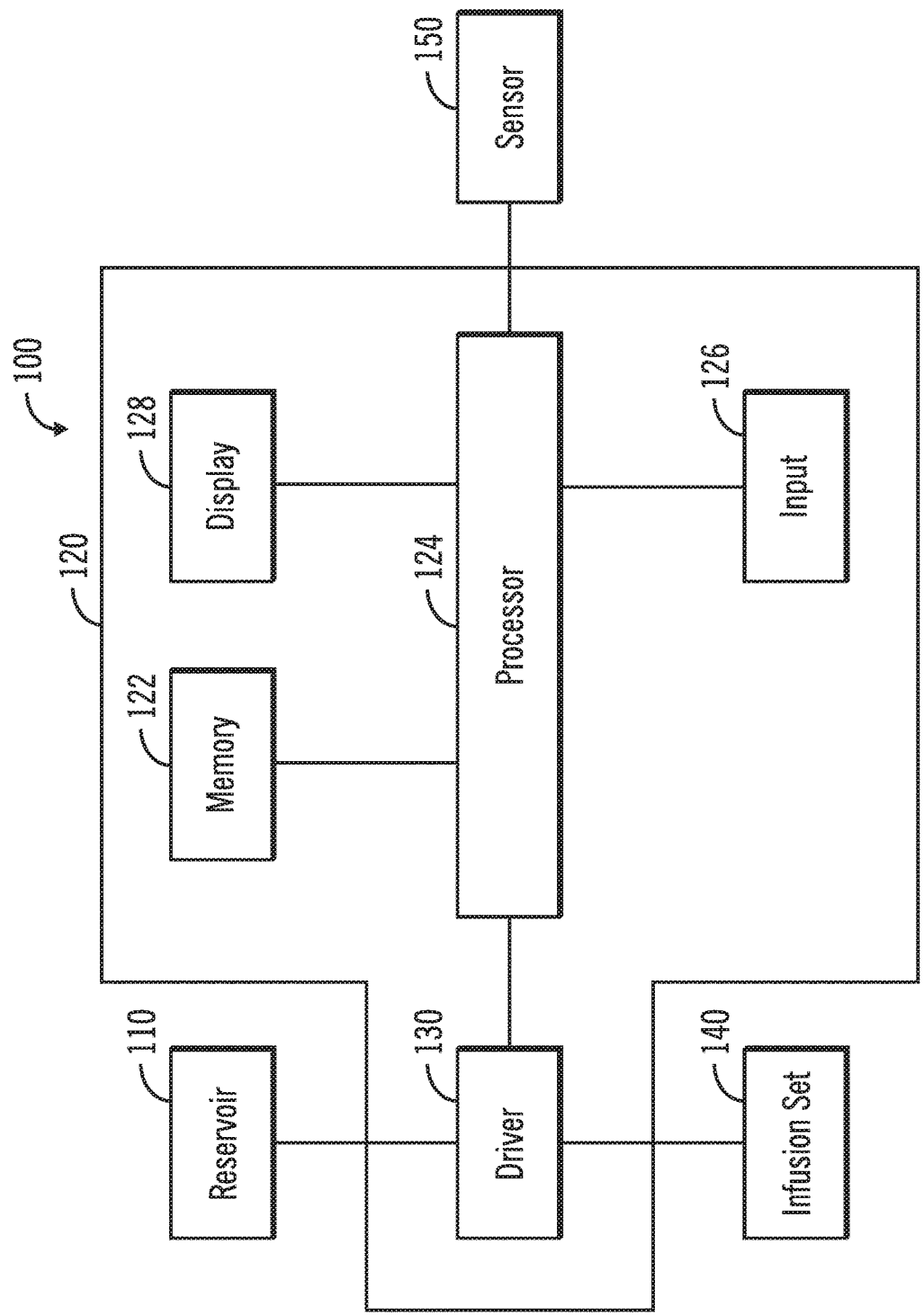
FIG. 1 is a block diagram of a personal medical system made in accordance with the invention.

FIG. 1 is a block diagram of a personal medical system made in accordance with the invention. The personal medical system 100 for providing a therapeutic fluid to a user includes a reservoir 110 containing the therapeutic fluid; a personal medical device 120 having a restricted mode, the personal medical device 120 being operably connected to the reservoir 110 to receive the therapeutic fluid; and an infusion set 140 operably connected to the personal medical device 120 to receive the therapeutic fluid. Those skilled in the art will appreciate that the fluidic connections illustrated are exemplary and that other configurations are equally possible, e.g., in other examples the infusion set 100 can be connected directly to the reservoir 110. The personal medical system 100 can optionally include a user sensor 150 to provide a sensed physiological signal from the user to the personal medical device 120. In one embodiment, the therapeutic fluid is insulin, the personal medical device 120 is an insulin pump, and the user sensor 150 is a glucose monitor.

The personal medical device 120 for employment by the user and having a restricted mode includes a memory 122 operable to store programming code; a processor 124 operably connected to the memory 122; a user input 126 operably connected to the processor 124 and having input buttons to receive input from the user; a user display 128 operably connected to the processor 124 to display output to the user; and a fluid driver 130 in fluid communication between the reservoir 110 and the infusion set 140, the fluid driver 130 being responsive to a flow control signal from the processor 124 to drive the therapeutic fluid from the reservoir 110 to the user through the infusion set 140.

The personal medical device 120 is prevented from entering a restricted mode, such as a mode in which the user can set or alter the therapy to be or being administered, without confirming that the user identifies a highlighted display button on the user display 128. A restricted mode is defined herein as any operational mode of the personal medical device 120 providing information or control to which restriction of access is desired: information about the user, information about therapy being administered to the user, and/or control of therapy being administered to the user. Exemplary restricted modes include the basal selection mode in which basal injection therapy can be selected and/or adjusted, and the bolus selection mode in which bolus injection therapy can be selected and/or adjusted. The processor 124 is responsive to the programming code stored in the memory 122 to detect a user request to request entry to the restricted mode; display a user input image on the user display 128 in response to the detected user request, the user input image including display buttons corresponding to the input buttons; highlight one of the display buttons; detect actuation of a second one of the input buttons on the user input 126; and deny entry to the restricted mode when the second one of the input buttons does not correspond to the highlighted one of the display buttons. The processor 124 can also be responsive to the programming code to permit entry to the restricted mode when the second one of the input buttons corresponds to the highlighted one of the display buttons. In one embodiment, the user request is actuation of an input button on the user input 126. In another embodiment, the user request is voice actuation such as when voice recognition is employed.

The processor 124 can also be operable to highlight the one of the display buttons as desired for a particular application. In one embodiment, the highlighting includes randomly highlighting the one of the display buttons. In another embodiment, the highlighting can follow a newly generated random sequence. For example, the newly generated random sequence of highlighted display buttons on subsequent challenge screens can be A, B, D, C with each letter corresponding to one of the display buttons and the user can key in the sequence of highlighted display buttons A, B, D, C to enter the restricted mode. This embodiment can be used by a care giver such a parent where the end user is not capable of making therapy decisions.

The personal medical device 120 can be any personal medical device for which presentation of a challenge screen before entry to a restricted mode is desired. In the particular example of FIG. 1, the personal medical device 120 is an insulin pump. In one example, the personal medical device 120 is an insulin pump and the restricted modes can be a basal selection mode and/or a bolus selection mode. Those skilled in the art will appreciate that the personal medical device 120 can be any personal medical device which delivers therapy to a patient and/or monitors a physiological parameter of the patient, as desired for a particular application. Exemplary personal medical devices include pumps, cell pumps, continuous glucose monitors, heart-rate monitors, ECG monitors, pulse oximeters, blood pressure monitors, respiration rate monitors, skin temperature monitors, electroencephalography (EEG) monitors, activity level monitors, vital sign monitors, and the like. The personal medical device as defined herein can be any medical device designed to be carried or worn by a user, including a memory, a processor, a user input, and a user display.

The processor 124 of the personal medical device 120 can be any processor desired for a particular application. Exemplary processors include a central processing unit and a microprocessor. The processor can include or be attached to auxiliary equipment, such as memory, data storage, additional processors, input/output devices, antennas, and the like, as required to perform various functions.

The user input 126 can include any type of input buttons desired for a particular application. In one embodiment, the input buttons can be electromechanical. In another embodiment, the user input 126 can be a touch-sensitive screen and the input buttons represented graphically on the touch-sensitive screen.

The user display 128 can be any type of display desired for a particular application, such as an LED display, an OLED display, an LCD display, or the like. In one embodiment, the user display 128 is a touch-sensitive display, with the user input 126 and the user display 128 included in the single touch-sensitive display. The input buttons of the user input 126 can be touch-sensitive buttons aligned with the display buttons of the user display 128 corresponding to the input buttons, so that the highlighted display button in the user input image appears on the same spot on the user display 128 as the corresponding input button.

The flow path for the therapeutic fluid is from the reservoir 110, through the driver 130, and through the infusion set 140 to the user. The reservoir 110 can be separate from, integral to, or replaceable within the housing of the personal medical device 120. In one embodiment, the reservoir 110 is a sealed vial replaceable within the personal medical device 120. In another embodiment, the reservoir 110 is refillable. The fluid driver 130 can be any type of pump operable to move the therapeutic fluid as desired for a particular application. The infusion set 140 can employ a cannula subcutaneously inserted in the user to deliver the therapeutic fluid. Those skilled in the art will appreciate that the fluidic connections illustrated are exemplary and that other configurations are equally possible, e.g., in other examples the infusion set 100 can be connected directly to the reservoir 110.

The user sensor 150 can be any sensor providing a sensed physiological signal from the user to the personal medical device 120. When the personal medical device 120 is an insulin pump, the user sensor 150 can be a glucose monitor. In one example, the user sensor 150 is a continuous glucose monitor. The user sensor 150 can be operably connected to the processor 124 by wire or wirelessly.

Figure 2A:
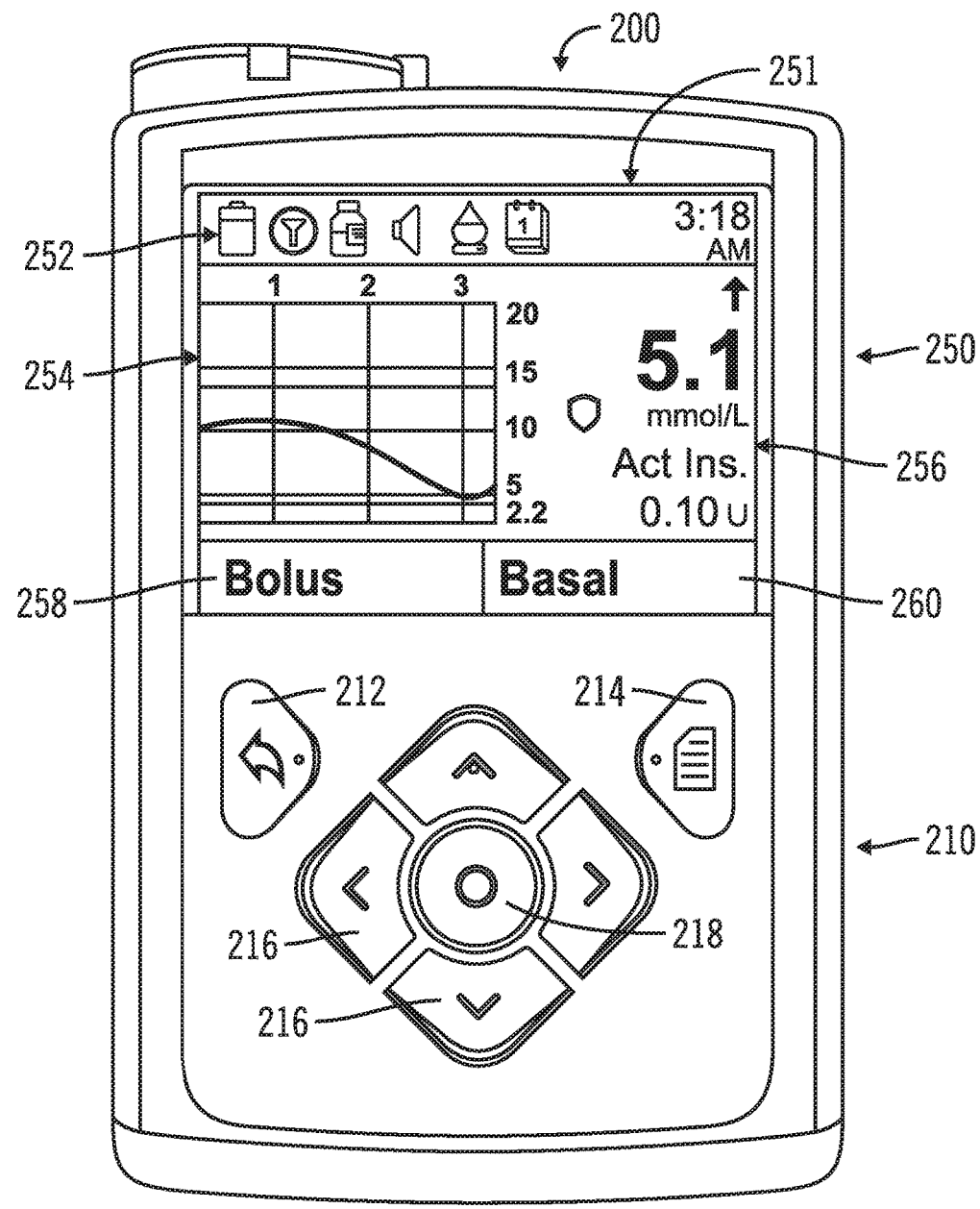
FIGS. 2A&2B are schematic diagrams of a personal medical device made in accordance with the invention.
Figure 2B:
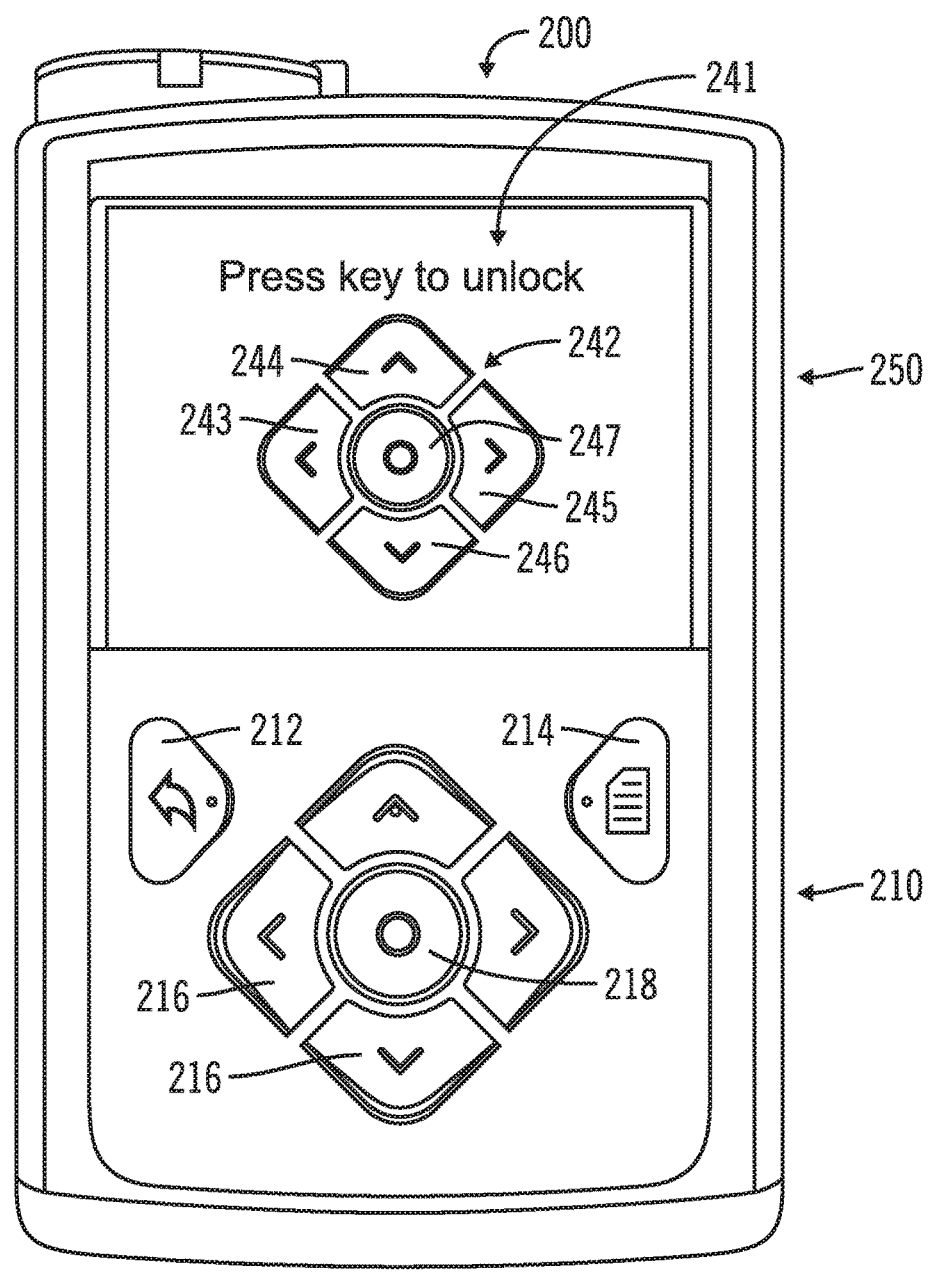

FIGS. 2A&2B are schematic diagrams of a personal medical device made in accordance with the invention. In this example, the personal medical device 200 is a portable infusion pump with a home screen displayed in the user display of the personal medical device in FIG. 2A and a challenge screen displayed in the user display of the personal medical device in FIG. 2B.

Referring to FIG. 2A, the personal medical device 200 includes a user input 210 to receive input from the user, and a user display 250 to display output to the user. In this example, the user display 250 displays a home screen. The user input 210 includes the following input buttons in this embodiment: back button 212, menu button 214, navigation buttons 216, and select button 218. The back button 212 shifts the user display 250 to the screen previously displayed on the user display 250. The menu button 214 brings up menu options on the user display 250. The navigation buttons 216 shift the focus between items displayed on the user display 250 to allow selection of an individual item through actuation of the select button 218. The individual item can be highlighted on the user display 250 to indicate that the individual item can be selected. The navigation buttons 216 (up, down, left, right) are arranged around the select button 218 in a diamond configuration for ease-of-use.

In this embodiment, the user display 250 displays a home screen 251 having a status bar 252, a sensed glucose graph 254, a numerical display 256, a first mode selection indication 258 (e.g., Bolus selection mode), and a second mode selection indication 260 (e.g., Basal selection mode). The status bar 252 can display information regarding the personal medical device 200, such as battery charge status, reservoir level, audio mode (audio and/or vibrate), and the like as desired for a particular application, and can be selectable to open a sub-menu. The status bar sub-menu can optionally be a restricted mode, presenting a challenge screen before access to the sub-menu is allowed. The sensed glucose graph 254 can display sensed glucose level versus time when a user sensor providing a sensed physiological signal, such as a glucose sensor, is used with the personal medical device 200. The numerical display 256 can display numerical and graphical information regarding physiological parameters and therapy being administered. The first mode selection indication 258 (e.g., Bolus selection mode) or the second mode selection indication 260 (e.g. Basal selection mode) can be highlighted to indicate the mode which will be entered when the user actuates the select button 218

The personal medical device 200 also includes a memory (not shown) operable to store programming code and a processor (not shown) operably connected to the memory. The user input 210 and the user display 250 are operably connected to the processor. The processor is responsive to the programming code to detect a user request to request entry to the restricted mode (a user request such as actuation of an input buttons on the user input 210, voice actuation, or the like); display a user input 210 image on the user display 250 in response to the detected user request, the user input 210 image including display buttons corresponding to the input buttons; highlight one of the display buttons; detect actuation of one of the input buttons on the user input 210; and deny entry to the restricted mode when the one of the input buttons does not correspond to the highlighted one of the display buttons. The processor can also be responsive to the programming code to permit entry to the restricted mode when the one of the input buttons corresponds to the highlighted one of the display buttons.

Referring to FIG. 2B, a challenge screen 241 is displayed in the user display 250 of the personal medical device 200. The challenge screen 241 can be displayed when the user attempts to enter a restricted mode, which is defined herein as any operational mode of the personal medical device 200 providing information or control to which restriction of access is desired: information about the user, information about therapy being administered to the user, and/or control of therapy being administered to the user. The challenge screen 241 includes a user input image 242, which has display buttons 243, 244, 245, 246, 247 on the user display 250 corresponding to the input buttons 216, 218 on the user input 210. In this example, the display buttons are the left navigation display button 243, up navigation display button 244, right navigation display button 245, down navigation display button 246, and select display button 247. The up navigation display button 244 is highlighted to indicate which input button on the user input the user must actuate to enter the restricted mode.

Those skilled in the art will appreciate that restricted modes can be selected as desired for a particular application, so that a challenge screen can be displayed to require that the user actuate an input button corresponding to a highlighted display button before the desired screen is displayed. Exemplary restricted modes include the basal selection mode in which basal injection therapy can be selected and/or adjusted, and the bolus selection mode in which bolus injection therapy can be selected and/or adjusted. In one example, menu select can be a restricted mode, i.e., when the user actuates the menu button 214, a challenge screen can be presented in the user display 250.

In another example, wake-from-sleep can be a restricted mode, i.e., when the user display 250 returns from a blank-display sleep mode to an active mode in response to actuation of an input button by the user, the user display 250 can present a challenge screen before any information is displayed. In yet another example, wake-from-sleep can be omitted as a restricted mode when the user had completed a challenge screen permitting entry to another restricted mode when the personal medical device went to sleep. In yet another example, wake-from-sleep can be omitted as a restricted mode and the user can be routed to the home screen to monitor status. In yet another example, specialized display can be a restricted mode, e.g., when the user actuates the select button 218 to display a large sensed glucose graph or detailed status, a challenge screen can be presented in the user display 250 before the specialized display is presented.

In another example, device-on can be a restricted mode, i.e., when the user turns on the personal medical device 200, the user display 250 can present a challenge screen which must be successfully completed by actuating an input button corresponding to a highlighted display button before the user can proceed to any other screen, such as the main menu screen, a screen providing information, a screen allowing user input or control, or the like. The user is denied entry past the challenge screen when the personal medical device 200 is initially turned on unless the challenge screen is successfully completed. In yet another example, device-on can be a restricted mode, but a screen providing information without allowing user input, such as a large sensed glucose graph or the like, can be displayed after the challenge screen has been displayed on the user display 250 for a predetermined time (challenge screen timeout), the user actuates an input button not corresponding to the highlighted display button (user fails challenge screen), the user actuates another button on the personal medical device 200 such as the back button or menu button (user selection), or the like.

FIGS. 3A-3D are schematic diagrams of bolus selection on a visual display of a personal medical device made in accordance with the invention. In this example, the restricted mode is the bolus selection mode.

Figure 3A:
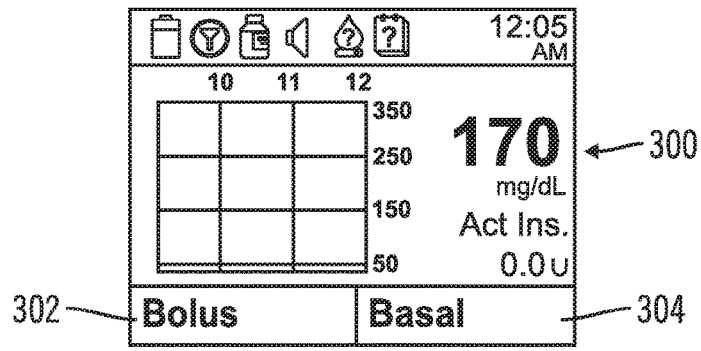
FIGS. 3A-3D are schematic diagrams of bolus selection on a visual display of a personal medical device made in accordance with the invention.

Referring to FIG. 3A, the user display of the personal medical device shows a home screen 300. The bolus selection indication 302 is highlighted and the basal selection indication 304 is un-highlighted to indicate that actuation of the select button will attempt to open the bolus selection mode. The bolus selection indication 302 can be highlighted by moving the highlighting from one field to another using the navigation buttons on the user input until the bolus selection indication 302 is highlighted.

Figure 3B:
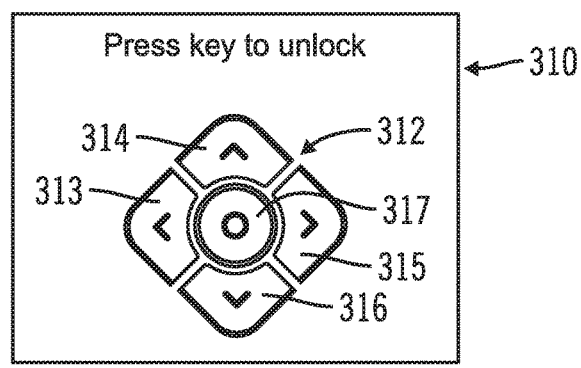

Referring to FIG. 3B, the user display of the personal medical device shows a challenge screen 310 in response to the user actuating the select button on the user input. The challenge screen 310 includes a user input image 312, which has display buttons on the user display corresponding to the input buttons on the user input. In this example, the display buttons are the left navigation display button 313, up navigation display button 314, right navigation display button 315, down navigation display button 316, and select display button 317. The down navigation display button 316 is highlighted to indicate which input button on the user input the user must actuate to enter the bolus selection mode.

Figure 3C:
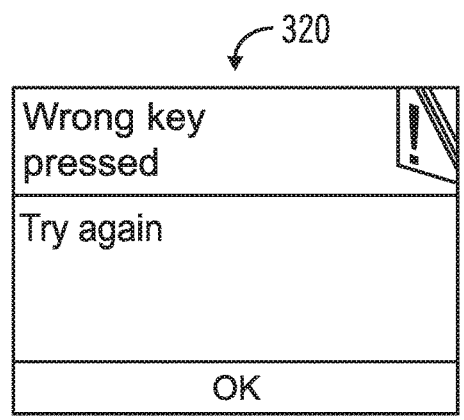

Referring to FIG. 3C, the user display of the personal medical device shows a challenge-failed screen 320 in response to the user actuating one of the input buttons on the user input other than the highlighted display button, such as the left navigation display button 313, up navigation display button 314, right navigation display button 315, or select display button 317, and not the highlighted down navigation display button 316. The user is denied entry to the restricted mode (bolus selection mode) because the actuated input button does not correspond to the highlighted display button. In one embodiment, the user can actuate the select button on the user input to return to the home screen as shown in FIG. 3A.

Figure 3D:
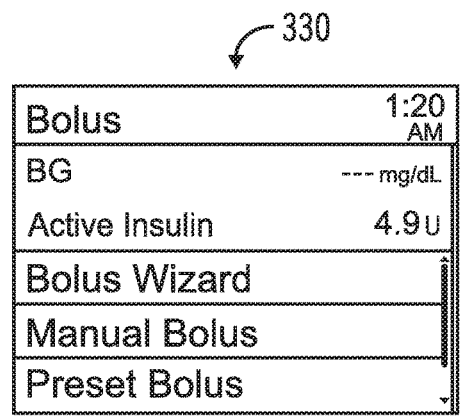

Referring to FIG. 3D, the user display of the personal medical device shows a bolus selection screen 330 in response to the user actuating the highlighted display button, i.e., the highlighted down navigation display button 316. The user is permitted entry to the restricted mode (bolus selection mode) because the actuated input button corresponds to the highlighted display button. The user can now proceed to program the bolus selection mode as desired under various protocols as allowed by the personal medical device. Those skilled in the art will appreciate that the challenge screen can be presented any time in the sequence prior to allowing the change in therapy, e.g., the challenge screen can be presented after selection of infusion parameters but as a final confirmation before permitting the selection to take effect. In this example, the restricted mode is final confirmation of the selection.

FIGS. 4A-4D are schematic diagrams of basal selection on a visual display of a personal medical device made in accordance with the invention. In this example, the restricted mode is the basal selection mode.

Figure 4A:
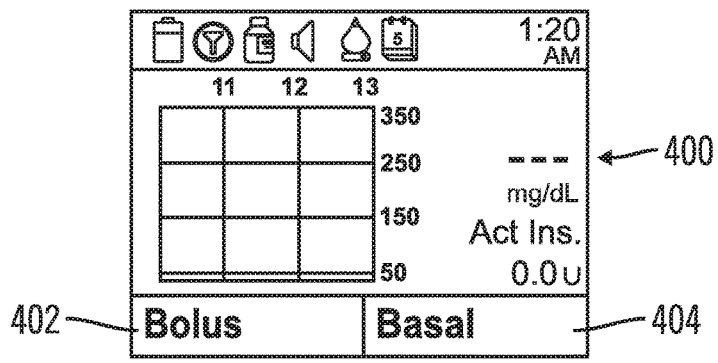
FIGS. 4A-4D are schematic diagrams of basal selection on a visual display of a personal medical device made in accordance with the invention.

Referring to FIG. 4A, the user display of the personal medical device shows a home screen 400. The bolus selection indication 402 is un-highlighted and the basal selection indication 404 is highlighted to indicate that actuation of the select button will attempt to open the basal selection mode. The basal selection indication 404 can be highlighted by moving the highlighting from one field to another using the navigation buttons on the user input until the basal selection indication 404 is highlighted.

Figure 4B:
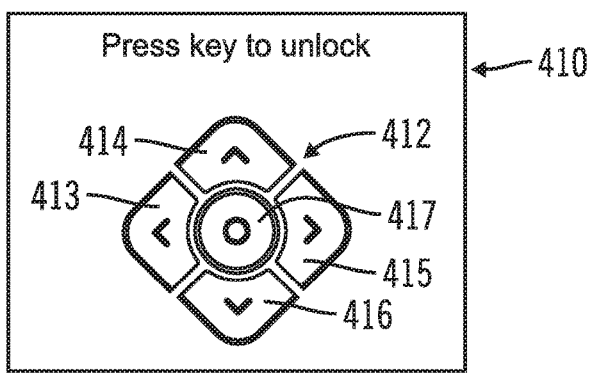

Referring to FIG. 4B, the user display of the personal medical device shows a challenge screen 410 in response to the user actuating the select button on the user input. The challenge screen 410 includes a user input image 412, which has display buttons on the user display corresponding to the input buttons on the user input. In this example, the display buttons are the left navigation display button 413, up navigation display button 414, right navigation display button 415, down navigation display button 416, and select display button 417. The down navigation display button 416 is highlighted to indicate which input button on the user input the user must actuate to enter the basal selection mode.

Figure 4C:
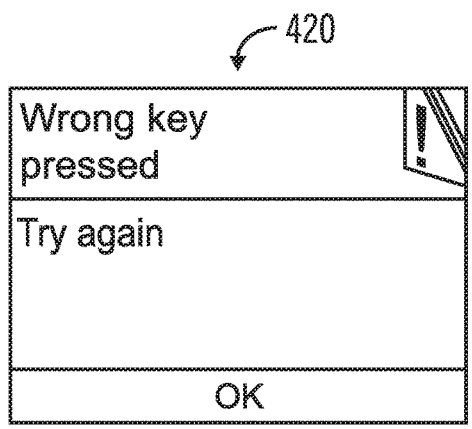

Referring to FIG. 4C, the user display of the personal medical device shows a challenge-failed screen 420 in response to the user actuating one of the input buttons on the user input other than the highlighted display button, such as the left navigation display button 413, up navigation display button 414, right navigation display button 415, or select display button 417, and not the highlighted down navigation display button 416. The user is denied entry to the restricted mode (basal selection mode) because the actuated input button does not correspond to the highlighted display button. In one embodiment, the user can actuate the select button on the user input to return to the home screen as shown in FIG. 4A.

Figure 4D:
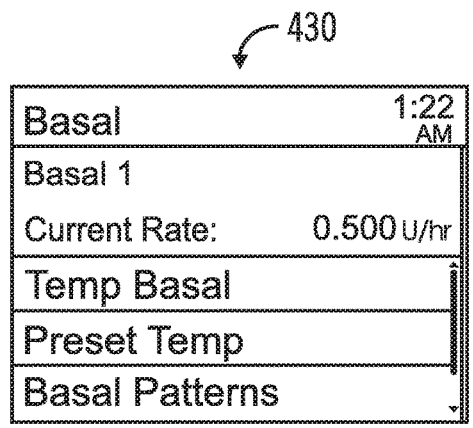

Referring to FIG. 4D, the user display of the personal medical device shows a basal selection screen 430 in response to the user actuating the highlighted display button, i.e., the highlighted down navigation display button 416. The user is permitted entry to the restricted mode (basal selection mode) because the actuated input button corresponds to the highlighted display button. The user can now proceed to program the basal selection mode as desired under various protocols as allowed by the personal medical device. Those skilled in the art will appreciate that the challenge screen can be presented any time in the sequence prior to allowing the change in therapy, e.g., the challenge screen can be presented after selection of infusion parameters but as a final confirmation before permitting the selection to take effect. In this example, the restricted mode is final confirmation of the selection.

FIGS. 5A-5D are schematic diagrams of menu selection on a visual display of a personal medical device made in accordance with the invention. In this example, the restricted mode is the menu selection mode.

Figure 5A:
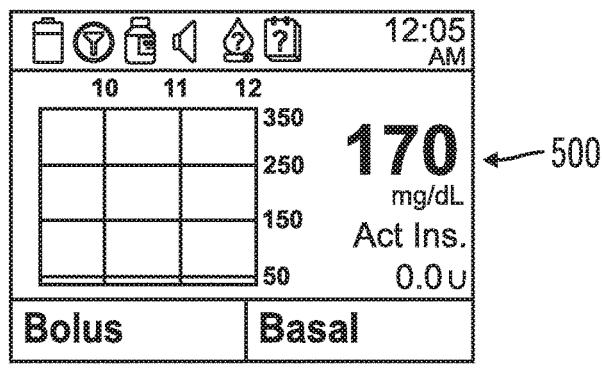
FIGS. 5A-5D are schematic diagrams of menu selection on a visual display of a personal medical device made in accordance with the invention.

Referring to FIG. 5A, the user display of the personal medical device shows a home screen 500. In this example, the menu selection mode is reached by actuation of the menu button on the user input.

Figure 5B:
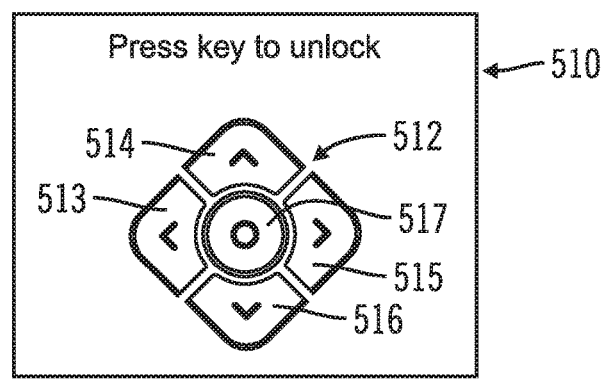

Referring to FIG. 5B, the user display of the personal medical device shows a challenge screen 510 in response to the user actuating the menu button on the user input. The challenge screen 510 includes a user input image 512, which has display buttons on the user display corresponding to the input buttons on the user input. In this example, the display buttons are the left navigation display button 513, up navigation display button 514, right navigation display button 515, down navigation display button 516, and select display button 517. The down navigation display button 516 is highlighted to indicate which input button on the user input the user must actuate to enter the menu selection mode.

Figure 5C:
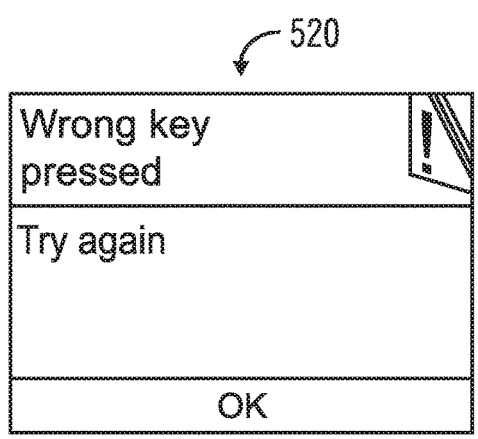

Referring to FIG. 5C, the user display of the personal medical device shows a challenge-failed screen 520 in response to the user actuating one of the input buttons on the user input other than the highlighted display button, such as the left navigation display button 513, up navigation display button 514, right navigation display button 515, or select display button 517, and not the highlighted down navigation display button 516. The user is denied entry to the restricted mode (menu selection mode) because the actuated input button does not correspond to the highlighted display button. In one embodiment, the user can actuate the select button on the user input to return to the home screen as shown in FIG. 5A.

Figure 5D:
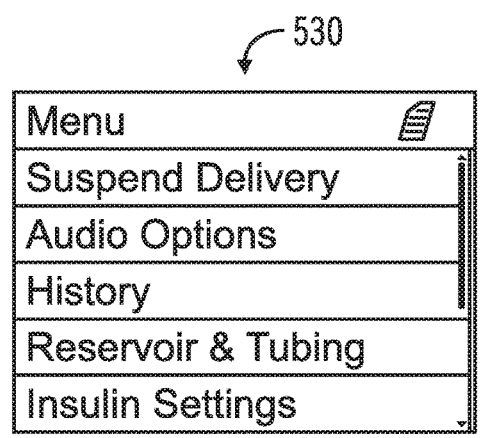

Referring to FIG. 5D, the user display of the personal medical device shows a menu selection screen 530 in response to the user actuating the highlighted display button, i.e., the highlighted down navigation display button 516. The user is permitted entry to the restricted mode (menu selection mode) because the actuated input button corresponds to the highlighted display button. The user can now proceed to program the menu selection mode as desired under various protocols as allowed by the personal medical device.

Figure 6:
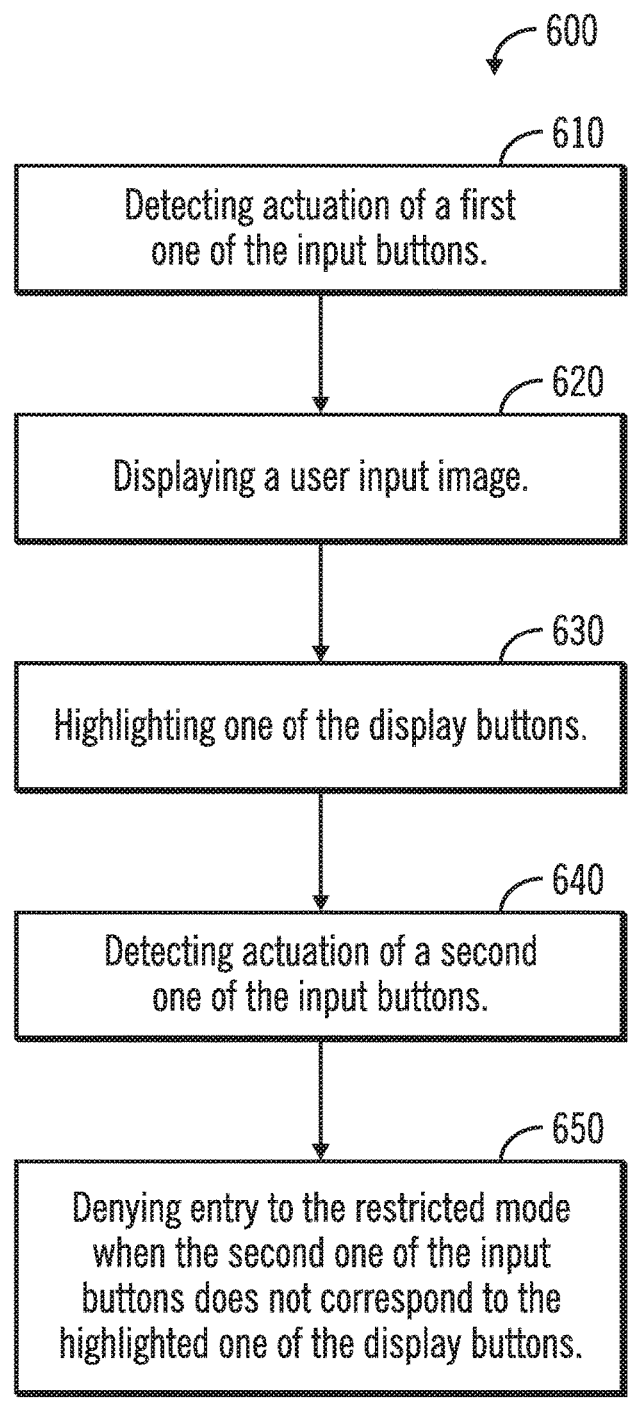
FIG. 6 is a flowchart for a method of use for a personal medical device made in accordance with the invention.

FIG. 6 is a flowchart for a method of use for a personal medical device made in accordance with the invention. The method 600 can be used with a personal medical device having a user display and a user input, with the user input having input buttons, as described in FIGS. 1&2. In one embodiment, a non-transitory computer readable medium can contain programming instructions for causing a personal medical device to perform the method 600 of FIG. 6.

Referring to FIG. 6, the method 600 of use for a personal medical device includes detecting a user request for entry to a restricted mode 610 of the personal medical device; displaying a user input image 620 on the user display in response to the detected user request, the user input image including display buttons corresponding to the input buttons; highlighting one of the display buttons 630; detecting actuation of one of the input buttons 640 on the user input; and denying entry to the restricted mode when the one of the input buttons does not correspond to the highlighted one of the display buttons 650. In one embodiment, the method 600 further includes permitting entry to the restricted mode when the one of the input buttons corresponds to the highlighted one of the display buttons. In one embodiment, the personal medical device can be an insulin pump and the restricted mode can be a basal selection mode and/or a bolus selection mode.

The highlighting one of the display buttons 630 can be performed as desired for a particular application. In one embodiment, the highlighting one of the display buttons 630 includes randomly highlighting the one of the display buttons. In another embodiment, the highlighting one of the display buttons 630 can follow a newly generated random sequence. For example, the newly generated random sequence of highlighted display buttons on subsequent challenge screens can be A, B, D, C with each letter corresponding to one of the display buttons and the user can key in the sequence of highlighted display buttons A, B, D, C to enter the restricted mode. This embodiment can be used by a care giver such a parent where the end user is not capable of making therapy decisions.

FIGS. 7A-7E, in which like elements share like reference numbers, are schematic diagrams of a personal medical device with a device-on restricted mode made in accordance with the invention. In this embodiment, device-on is a restricted mode, i.e., when the user turns on the personal medical device, the user display presents a challenge screen which must be successfully completed by actuating an input button corresponding to a highlighted display button before the user can proceed to a screen allowing user input or control. In this example, device-on is a restricted mode, but a screen providing information without allowing user input, such as a large sensed glucose graph, a locked information screen, or the like, is displayed when the user actuates an input button on the user input.

Figure 7A:
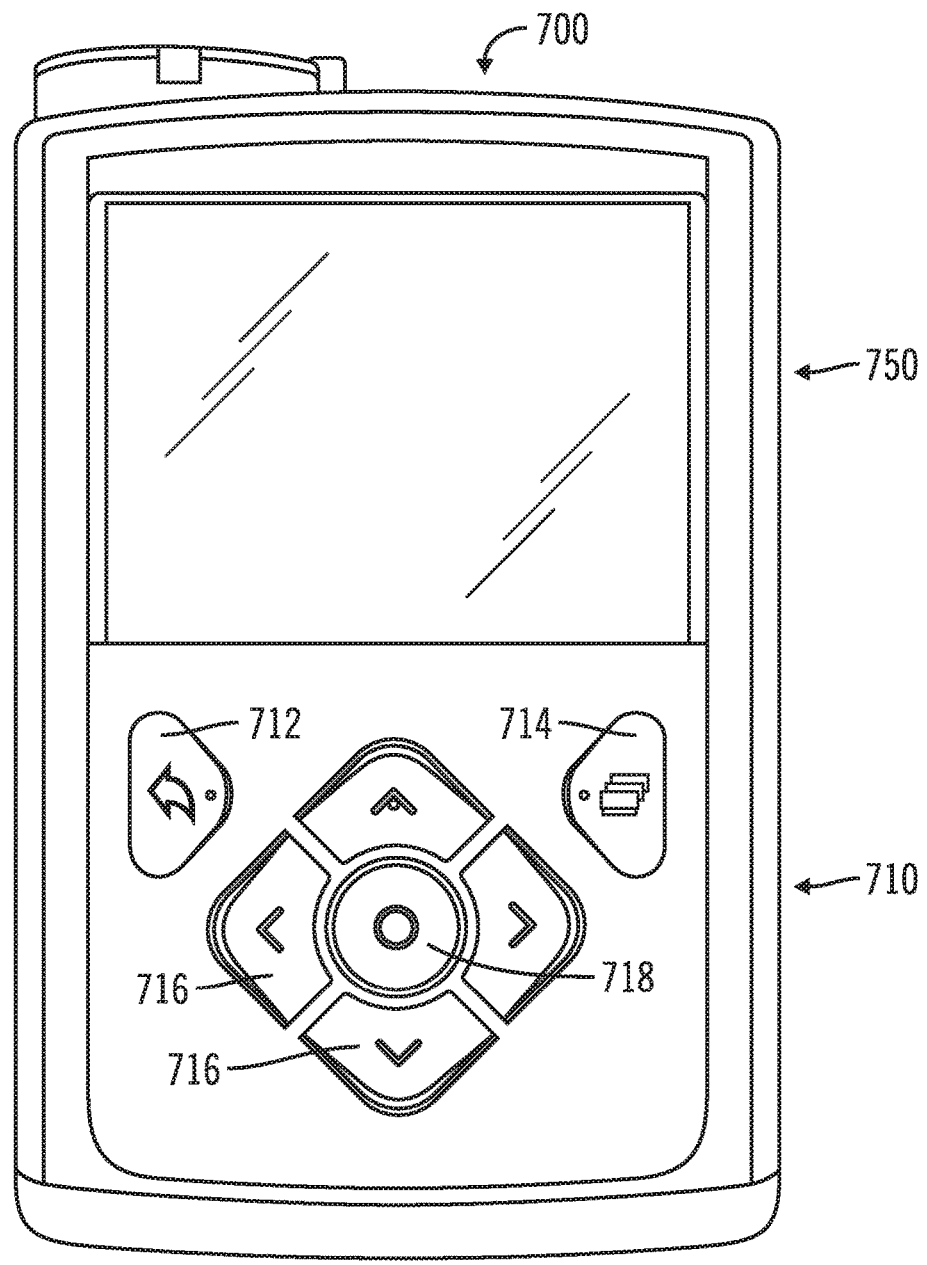
FIGS. 7A-7E are schematic diagrams of a personal medical device with a device-on restricted mode made in accordance with the invention.

Referring to FIG. 7A, the personal medical device 700 includes a user input 710 to receive input from the user, and a user display 750 to display output to the user. In this example, the personal medical device 700 is in a device-off state, so the user display 750 displays a blank screen. The user input 710 includes the following input buttons in this embodiment: back button 712, menu button 714, navigation buttons 716, and select button 718. The navigation buttons 716 (up, down, left, right) are arranged around the select button 718 in a diamond configuration for ease-of-use.

Figure 7B:
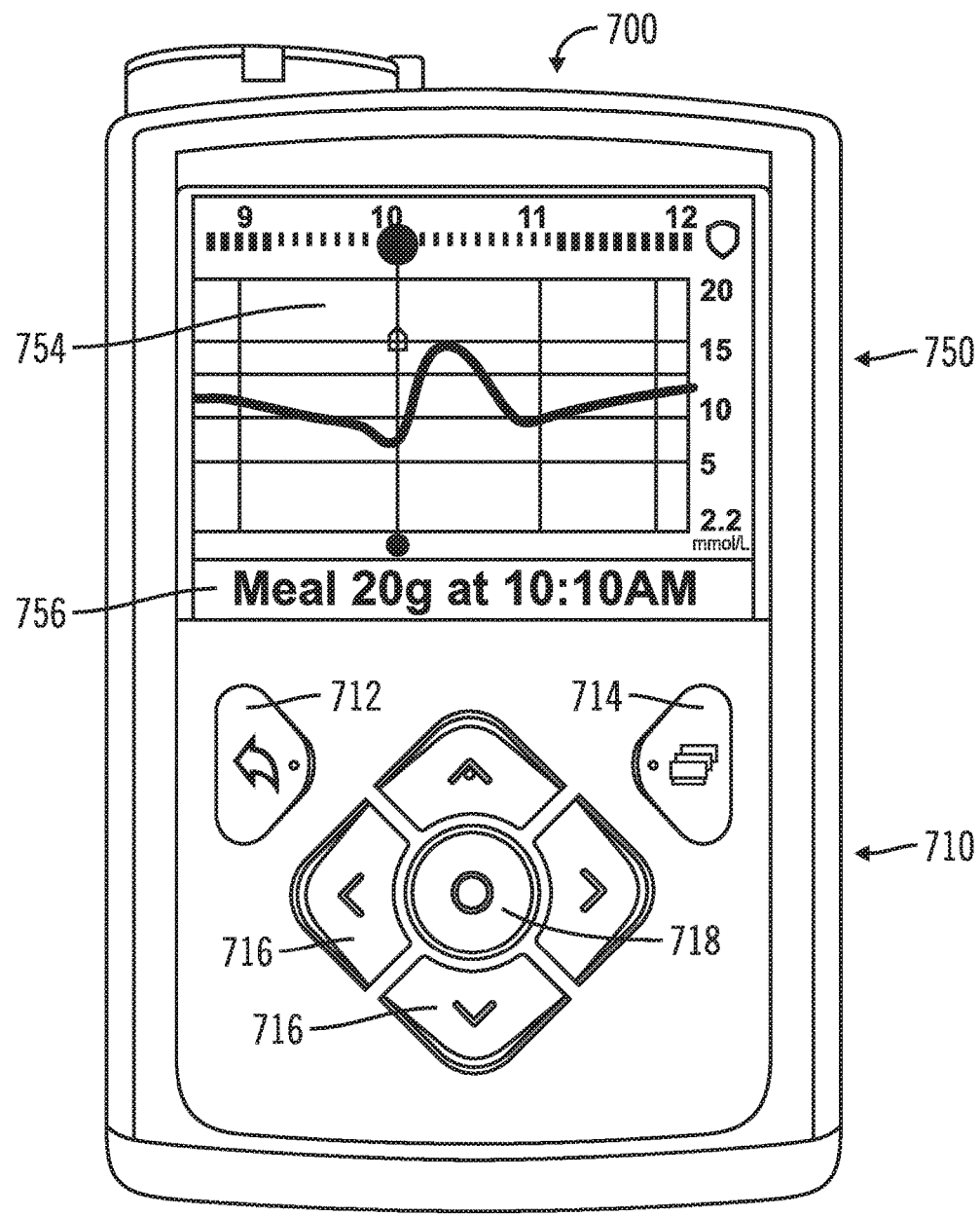

Referring to FIG. 7B, the user display 750 of the personal medical device 700 displays a large sensed glucose graph 754. The large sensed glucose graph 754 appears when the user actuates the menu button 714 with the personal medical device 700 in the device-off state illustrated in FIG. 7A. In the example illustrated in FIG. 7B, the user display 750 also displays event information 756 indicating recent activity of interest. Actuating the menu button 714 when the large sensed glucose graph 754 is displayed switches the user display 750 to the locked information screen 764 as illustrated in FIG. 7C.

Figure 7C:
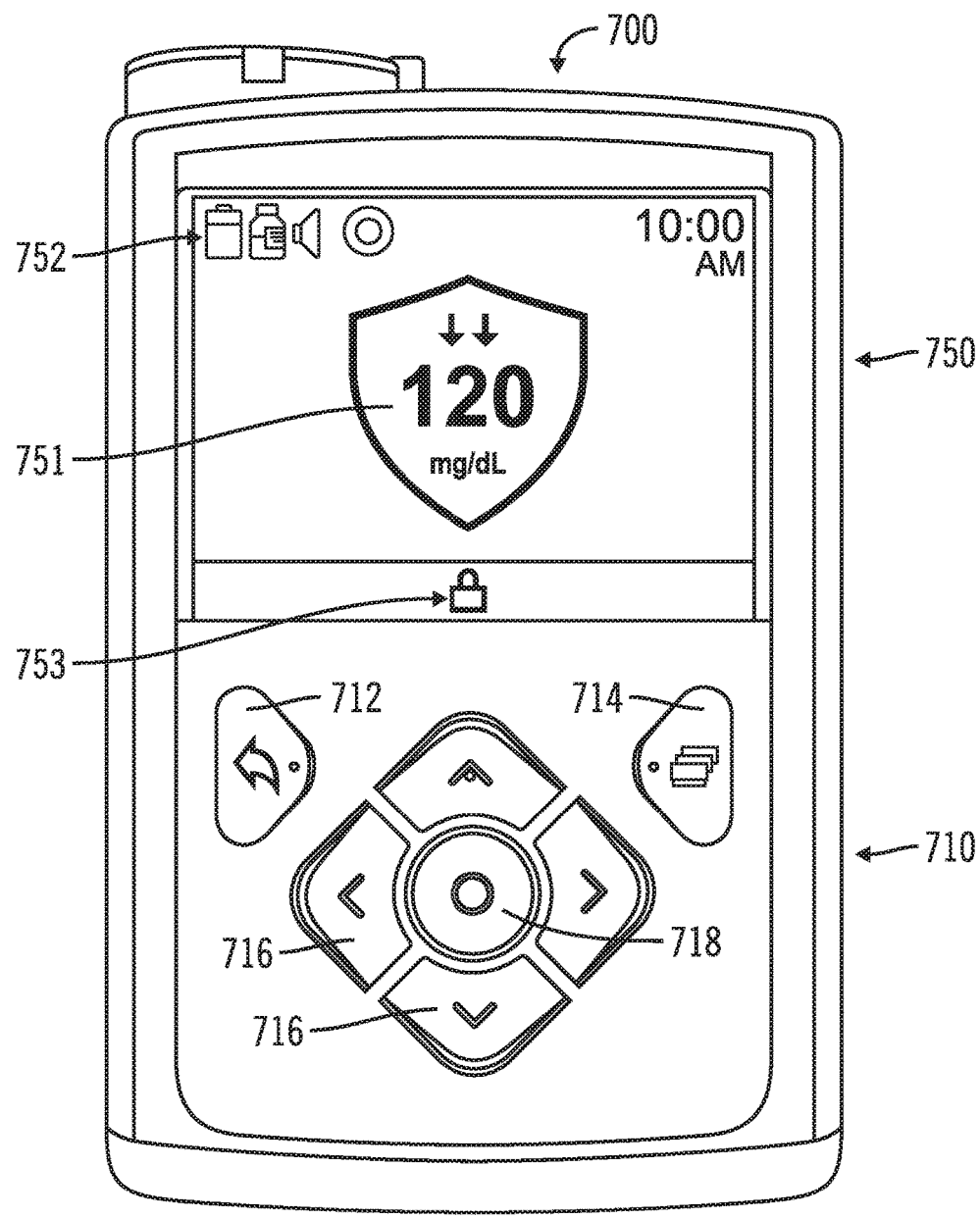

Referring to FIG. 7C, the user display 750 of the personal medical device 700 displays a locked information screen 764, at which no user input or control is allowed. The locked information screen 764 appears when the user actuates one of the back button 712, navigation buttons 716, or select button 718 with the personal medical device 700 in the device-off state illustrated in FIG. 7A. In the example illustrated in FIG. 7C, the user display 750 displays a status bar 752, infusion rate 751, and locked indicator 753 that indicates no user input or control is allowed. Actuating the menu button 714 switches the user display 750 to the large sensed glucose graph as illustrated in FIG. 7B, while actuating the select button 718 switches the user display 750 to a challenge screen as illustrated in FIG. 7D.

Figure 7D:
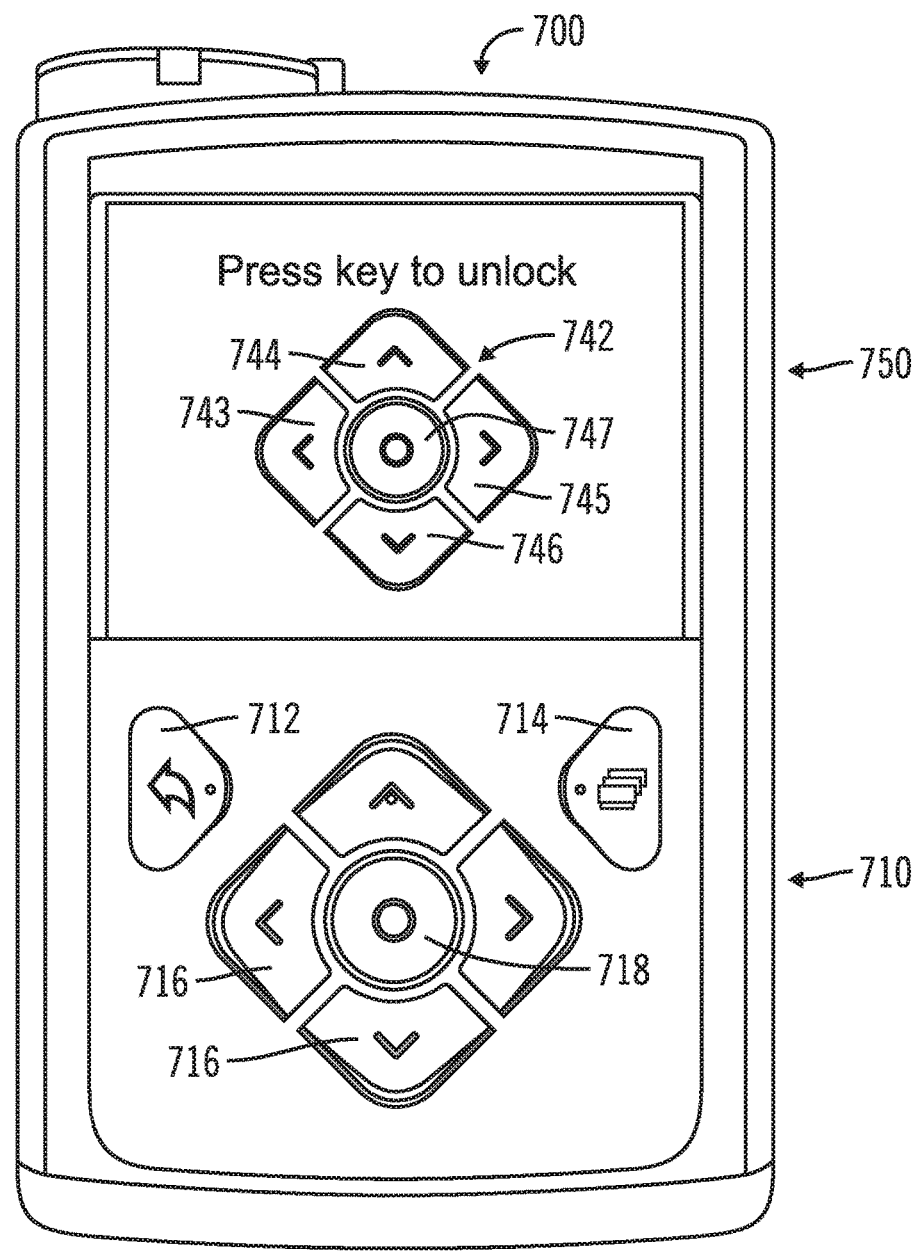
Figure 7E:
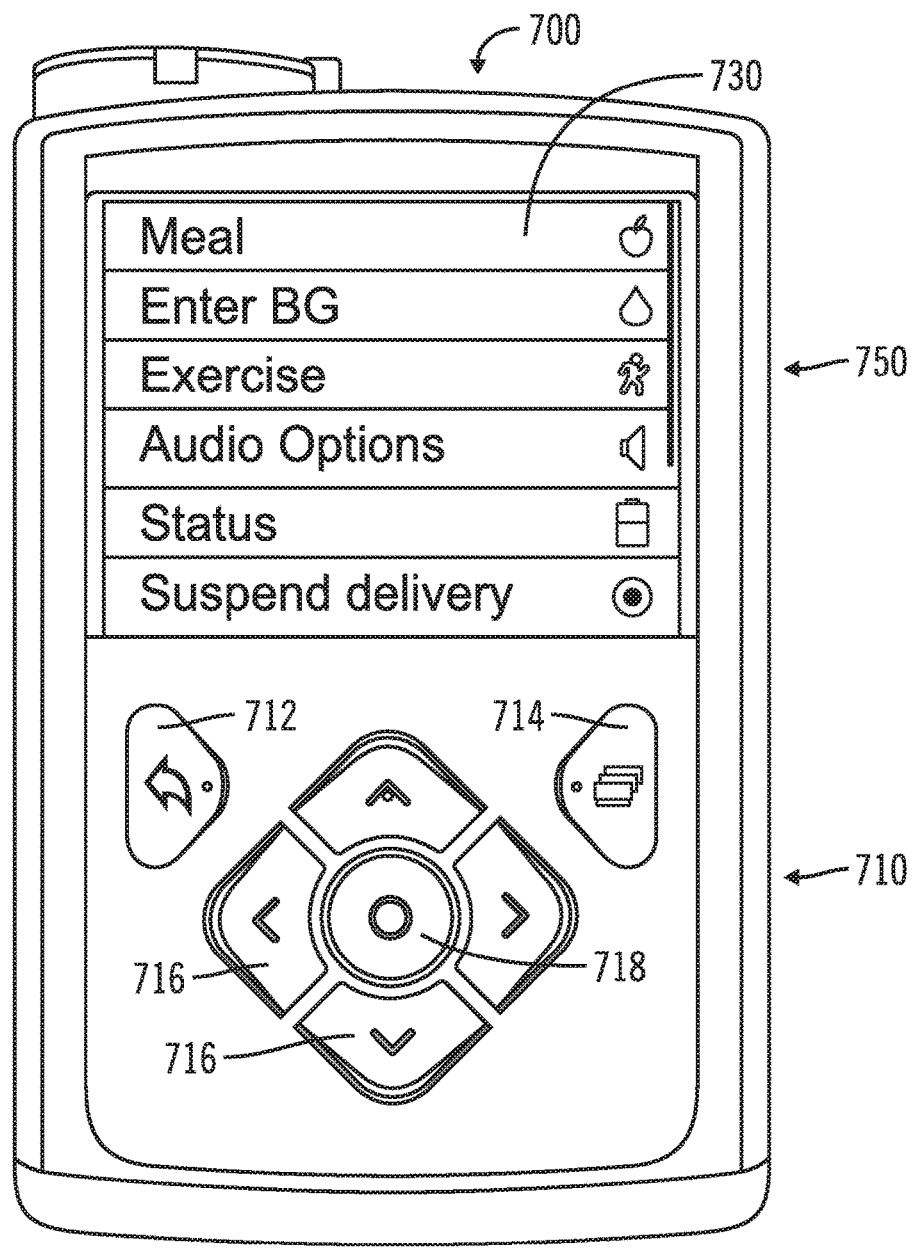

Referring to FIG. 7D, the user display 750 of the personal medical device 700 displays a challenge screen 741, which is displayed when the user attempts to enter a restricted mode that in this example is the device-on restricted mode. The challenge screen 741 includes a user input image 742, which has display buttons 743, 744, 745, 746, 747 on the user display 750 corresponding to the input buttons 716, 718 on the user input 710. In this example, the display buttons are the left navigation display button 743, up navigation display button 744, right navigation display button 745, down navigation display button 746, and select display button 747. The down navigation display button 746 is highlighted to indicate which input button on the user input the user must actuate to enter the restricted mode. Actuating the input button 716 corresponding to the highlighted down navigation display button 746, in this example the down input button 716, switches the user display 750 to a menu selection screen as illustrated in FIG. 7E and permits the user to enter the restricted mode. Actuating an input button 716 other than the input button corresponding to the highlighted down navigation display button 746, in this example the down input button 716, switches the user display 750 to the locked information screen 764 as illustrated in FIG. 7C. Those skilled in the art will appreciate that other screens can be displayed on the user display 750 as desired for a particular application when the user fails to select the input button corresponding to the highlighted display button.

Referring to FIG. 7E, the user display 750 of the personal medical device 700 displays a menu selection screen 730 at which user input or control is allowed. In this example, the user can select from a number of options, such as Meal, enter BG (Blood Glucose), Exercise, Audio Options, Status, or Suspend delivery, and proceed to program the personal medical device 700 as desired under various protocols as allowed by the personal medical device. The navigation buttons 716 shift the focus between options displayed on the user display 750 to allow selection of an individual option through actuation of the select button 718. The individual option can be highlighted on the user display 750 to indicate that the individual option can be selected.

It is important to note that FIGS. 1-7 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A personal medical device for employment by a user and having a restricted mode, the personal medical device comprising:
   a memory operable to store programming code;
   a processor operably connected to the memory;
   a user input operably connected to the processor and having input buttons to receive input from the user; and
   a user display operably connected to the processor to display output to the user;
   wherein the processor is responsive to the programming code to:
      detect a user request for entry to the restricted mode;
      display a user input image on the user display in response to the detected user request, the user input image including display buttons corresponding to the input buttons;
      highlight one of the display buttons;
      detect actuation of one of the input buttons on the user input; and
      deny entry to the restricted mode when the one of the input buttons does not correspond to the highlighted one of the display buttons;
      wherein the processor being operable to highlight one of the display buttons further comprises the processor being operable to randomly highlight the one of the display buttons.

2. The personal medical device of claim 1 wherein the processor is further responsive to the programming code to permit entry to the restricted mode when the one of the input buttons corresponds to the highlighted one of the display buttons.

3. The personal medical device of claim 1 wherein the user request is selected from the group consisting of actuation of an input button on the user input and voice actuation.

4. The personal medical device of claim 1 for use with an infusion set and a reservoir containing a therapeutic fluid, the personal medical device further comprising a fluid driver in communication between the reservoir and the infusion set, the fluid driver being responsive to a flow control signal from the processor to drive the therapeutic fluid from the reservoir to the user through the infusion set.

5. The personal medical device of claim 1 wherein the restricted mode is selected from the group consisting of a basal selection mode and a bolus selection mode.

6. The personal medical device of claim 1 further comprising a user sensor operably connected to the processor and the user to provide a sensed physiological signal from the user.

7. The personal medical device of claim 1 wherein the user input and the user display are included in a single touch-sensitive display, the input buttons of the user input being touch-sensitive buttons and being aligned with the display buttons of the user display corresponding to the input buttons.

8. A personal medical system for providing a therapeutic fluid to a user, the personal medical system comprising:
   a reservoir containing the therapeutic fluid;
   a personal medical device having a restricted mode, the personal medical device being operably connected to the reservoir to receive the therapeutic fluid; and
   an infusion set operably connected to the personal medical device to receive the therapeutic fluid;
   wherein the personal medical device further comprises:
      a memory operable to store programming code;
      a processor operably connected to the memory;
      a user input operably connected to the processor and having input buttons to receive input from the user;
      a user display operably connected to the processor to display output to the user; and
      a fluid driver in communication between the reservoir and the infusion set, the fluid driver being responsive to a flow control signal from the processor to drive the therapeutic fluid from the reservoir to the user through the infusion set;
      wherein the processor is responsive to the programming code to:
         detect a user request for entry to the restricted mode;
         display a user input image on the user display in response to the detected user request, the user input image including display buttons corresponding to the input buttons;
         highlight one of the display buttons;
         detect actuation of one of the input buttons on the user input; and
         deny entry to the restricted mode when the one of the input buttons does not correspond to the highlighted one of the display buttons;
         wherein the processor being operable to highlight one of the display buttons further comprises the processor being operable to randomly highlight the one of the display buttons.

9. The personal medical system of claim 8 wherein the processor is further responsive to the programming code to permit entry to the restricted mode when the one of the input buttons corresponds to the highlighted one of the display buttons.

10. The personal medical system of claim 8 wherein the user request is selected from the group consisting of actuation of an input button on the user input and voice actuation.

11. The personal medical system of claim 8 wherein the restricted mode is selected from the group consisting of a basal selection mode and a bolus selection mode.

12. The personal medical system of claim 8 further comprising a user sensor operably connected to the processor and the user to provide a sensed physiological signal from the user.

13. The personal medical system of claim 12 wherein the therapeutic fluid is insulin, the personal medical device is an insulin pump, and the user sensor is a glucose monitor.

14. The personal medical system of claim 8 wherein the user input and the user display are included in a single touch-sensitive display, the input buttons of the user input being touch-sensitive buttons and being aligned with the display buttons of the user display corresponding to the input buttons.

15. A method of use for a personal medical device having a user display and a user input, the user input having input buttons, the method comprising:

detecting a user request for entry to a restricted mode of the personal medical device;

displaying a user input image on the user display in response to the detected user request, the user input image including display buttons corresponding to the input buttons;

highlighting one of the display buttons;

detecting actuation of one of the input buttons on the user input; and denying entry to the restricted mode when the one of the input buttons does not correspond to the highlighted one of the display buttons;

wherein the highlighting comprises randomly highlighting the one of the display buttons.

16. The method of claim 15 further comprising permitting entry to the restricted mode when the one of the input buttons corresponds to the highlighted one of the display buttons.

17. The method of claim 15 wherein the restricted mode is selected from the group consisting of a basal selection mode and a bolus selection mode.

* * * * *